United States Patent
Hong et al.

(10) Patent No.: US 12,360,511 B2
(45) Date of Patent: Jul. 15, 2025

(54) AUTOMATED CHEMICAL FORMULATION APPARATUS AND METHOD THEREOF

(71) Applicant: KOREA ADVANCED INSTITUTE OF SCIENCE AND TECHNOLOGY, Daejeon (KR)

(72) Inventors: Seung Bum Hong, Daejeon (KR); Chi Hao Liow, Daejeon (KR); Young Woo Choi, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 867 days.

(21) Appl. No.: 17/508,111

(22) Filed: Oct. 22, 2021

(65) Prior Publication Data
US 2022/0397886 A1 Dec. 15, 2022

(30) Foreign Application Priority Data
Jun. 4, 2021 (KR) .......... 10-2021-0072776

(51) Int. Cl.
*G05B 19/4155* (2006.01)
*G06N 20/00* (2019.01)

(52) U.S. Cl.
CPC ......... *G05B 19/4155* (2013.01); *G06N 20/00* (2019.01); *G05B 2219/32287* (2013.01)

(58) Field of Classification Search
CPC ........ G16C 20/10; G16C 20/70; G16C 60/00; G05B 19/4155; G05B 2219/32287;
(Continued)

(56) References Cited

U.S. PATENT DOCUMENTS 6,546,295 B1 * 4/2003 Pyotsia .............. G05B 19/4185
706/900
6,597,958 B1 * 7/2003 Starr .................. G05B 23/0243
703/2
(Continued)

FOREIGN PATENT DOCUMENTS

KR 10-2007-0053705 A 5/2007

*Primary Examiner* — Shogo Sasaki
(74) *Attorney, Agent, or Firm* — Bridgeway IP Law Group, PLLC; Jihun Kim

(57) ABSTRACT

An automated chemical formulation apparatus includes: a data reception unit that receives an input chemical material dataset including chemical material information, chemical composition information, chemical formulation information and property information thereof; a predicting model generation unit that trains a first machine learning model using the input chemical material dataset to generate a predicting model for predicting a chemical formulation based on target property information of a target material; and a formulation prediction unit that sets a boundary condition based on the input chemical material dataset, generates a new input dataset including at least one of chemical material information, chemical composition information, and chemical formulation information within the boundary condition, inputs the new input dataset to the predicting model, and sets predetermined one or more pieces of target property information to perform prediction, thereby outputting a first group of chemical formulation data.

13 Claims, 6 Drawing Sheets

(58) Field of Classification Search
CPC ........ G06N 20/00; G06N 20/10; G06N 20/20; G06N 5/01
See application file for complete search history.

(56) References Cited

U.S. PATENT DOCUMENTS

| | | | | |
|---|---|---|---|---|
| 9,529,348 | B2* | 12/2016 | Kephart | G05B 17/02 |
| 10,545,482 | B2* | 1/2020 | Dash | G05B 17/02 |
| 11,853,032 | B2* | 12/2023 | Chan | G05B 19/4155 |
| 11,857,939 | B2* | 1/2024 | Lusk | G05B 13/048 |
| 2004/0260421 | A1* | 12/2004 | Persson | D21G 9/0018 |
| | | | | 162/263 |
| 2016/0026171 | A1* | 1/2016 | Dash | G05B 17/02 |
| | | | | 700/267 |
| 2018/0353925 | A1 | 12/2018 | Giiazov et al. | |
| 2020/0012265 | A1* | 1/2020 | Thomsen | G06F 3/0481 |
| 2020/0379442 | A1* | 12/2020 | Chan | B01J 19/0033 |
| 2022/0072500 | A1* | 3/2022 | Lusk | C02F 1/686 |
| 2022/0260980 | A1* | 8/2022 | Andreu | G06N 20/00 |

* cited by examiner

AUTOMATED CHEMICAL FORMULATION APPARATUS AND METHOD THEREOF

BACKGROUND OF THE INVENTION

Field of the Invention

The present invention relates to an automated chemical formulation and method, and more particularly relates to an automated chemical formulation apparatus and method for deriving and synthesizing chemical formulation based on artificial intelligence that breaks away from the traditional experiment-based, time-consuming trial-and-error formulation search aiming at finding an optimized formulation that exhibit a desired physical property.

Description of the Related Art

Recently, artificial intelligence (AI) technology has been used to solve various problems by learning from data so that the design and synthesis of drugs and substances can be performed in a less time-consuming manner in fields such as chemistry and medicine.

Korean Patent Publication No. 2007-7002716 discloses a technology for predicting properties according to chemical mixture components using an artificial neural network model. However, this technology has a problem in that a researcher needs to directly perform some work steps to predict and design chemical mixture components.

Accordingly, recently, a technology that makes it easier to design a compound structure of a small molar unit by applying big data and machine learning to quantum chemistry has been actively studied.

However, in these conventional technologies, it is difficult to execute the formulation search using the time-consuming trial- and error-method based on traditional experimental methods, and there is a limitation that even after designing a synthetic composition or a molar structure of a compound through machine learning, the compound can be used in manufacture, only after going through a process of actual physical property validation experimentally.

CITATION LIST

Patent Literature

Korean Patent Literature 1: KR 10-2007-0053705 A

SUMMARY OF THE INVENTION

The present invention has been proposed to solve the above problems, and an object of the present invention is to provide an AI-based automated chemical formulation apparatus and method allowing both derivation and validation of a chemical formulation exhibiting a desired target property while minimizing or not requiring a trial-and-error search such as a search based on empirical rules of researchers or a time-consuming and expensive experiment in deriving the chemical formulation.

In addition, an object of the present invention is to provide an accurate, efficient, and economical AI-based automated chemical formulation apparatus and method capable of deriving and validating chemical formulation and directly applying the proven chemical formulation to a dispensing device for synthesis of the chemical material to produce the chemical material.

To achieve the above objects, an automated chemical formulation apparatus according to an embodiment of the present invention includes
- a data reception unit that receives a first chemical material dataset including chemical material information, chemical composition information, chemical formulation information and property information thereof;
- a predicting model generation unit that trains a first machine learning model using the input chemical material dataset to generate a predicting model for predicting a chemical formulation based on target property information of a target material;
- a formulation prediction unit that sets a boundary condition based on the first chemical material dataset, generates a new input dataset including the chemical material information, chemical composition information, and chemical formulation information within the boundary condition, inputs the new input dataset to the predicting model, and sets predetermined one or more pieces of target property information to perform prediction, thereby outputting chemical formulation data of a first group;
- a validation model generation unit that trains a second machine learning model different from the first machine learning model using the first chemical material dataset to generate a validation model;
- a validation formulation prediction unit that inputs the new input dataset to the validation model, and sets the predetermined one or more pieces of target property information to perform prediction, thereby outputting a second group of chemical formulation data; and
- a validation unit that compares and verifies the first group of chemical formulation data with the second group of chemical formulation data to derive matching data as chemical formulation data of a third group corresponding to the predetermined one or more pieces of target property information.

The automated chemical formulation apparatus may further include a chemical dispensing device that supplies and reacts component materials stored in individual chemical repositories based on the selected chemical formulation data of the third group to synthesize a target chemical material.

The automated chemical formulation apparatus may further include an inspection device that inspects a property of the synthesized target chemical material.

When setting the boundary condition, the formulation prediction unit may set boundary conditions that are maximum and minimum values of a predetermined chemical material input feature.

The formulation prediction unit may generate the new input dataset using a pseudo-random number generator (pRDG) within the predetermined boundary condition.

The chemical material dataset may be reduced in dimension and complexity of input data by weighting using feature importance or principal component analysis (PCA).

The first machine learning model may use one of a support vector machine (SVM) or XGboost (XGB).

The chemical dispensing device may include a control unit and a dispensing pump, and the control unit may perform a control operation to supply the component materials through the dispensing pump based on the third group of chemical formulation data.

An automated chemical formulation method performed by a computing device according to another embodiment of the present invention includes:
- receiving a first chemical material dataset including chemical material information, chemical composition information, chemical formulation information and property information thereof;

training a first machine learning model using the input chemical material dataset to generate a predicting model for predicting a chemical formulation based on target property information of a target material;

setting a boundary condition based on the input chemical material dataset and generating a new input dataset including at least one of chemical material information, chemical composition information, and chemical formulation information within the boundary condition;

inputting the new input dataset to the predicting model and setting predetermined one or more pieces of target property information to perform prediction, thereby outputting chemical formulation data of a first group;

training a second machine learning model different from the first machine learning model using the same input chemical material dataset to generate a validation model;

inputting the new input dataset to the validation model and setting the predetermined one or more pieces of target property information to perform prediction, thereby outputting a second group of chemical formulation data; and comparing and verifying the first group of chemical formulation data with the second group of chemical formulation data to derive matching data as chemical formulation data of a third group corresponding to the predetermined one or more pieces of target property information.

The automated chemical formulation method may further include supplying and reacting component materials stored in individual chemical repositories based on the selected chemical formulation data of the third group to synthesize the predicted chemical material by a chemical dispensing device.

The automated chemical formulation method may further include inspecting a property of the synthesized chemical material.

The generating of the new input dataset may include setting boundary conditions that are maximum and minimum values of a predetermined chemical feature.

The generating of the new input dataset may include generating the new input dataset using a pRDG within the boundary condition.

The input chemical material dataset may be reduced in dimension and complexity of input data by weighting a principal variable or a principal component using feature importance or PCA.

The first machine learning model may use one of an SVM or XGB.

The chemical dispensing device may include a control unit and a dispensing pump, and the control unit may perform a control operation to supply the component materials through the dispensing pump based on the third group of chemical formulation data.

According to an embodiment of the present invention, a computer-readable storage medium on which a program for performing the automated chemical formulation method is stored may be included.

DETAILED DESCRIPTION OF THE PREFERRED EMBODIMENTS

Figure 1:
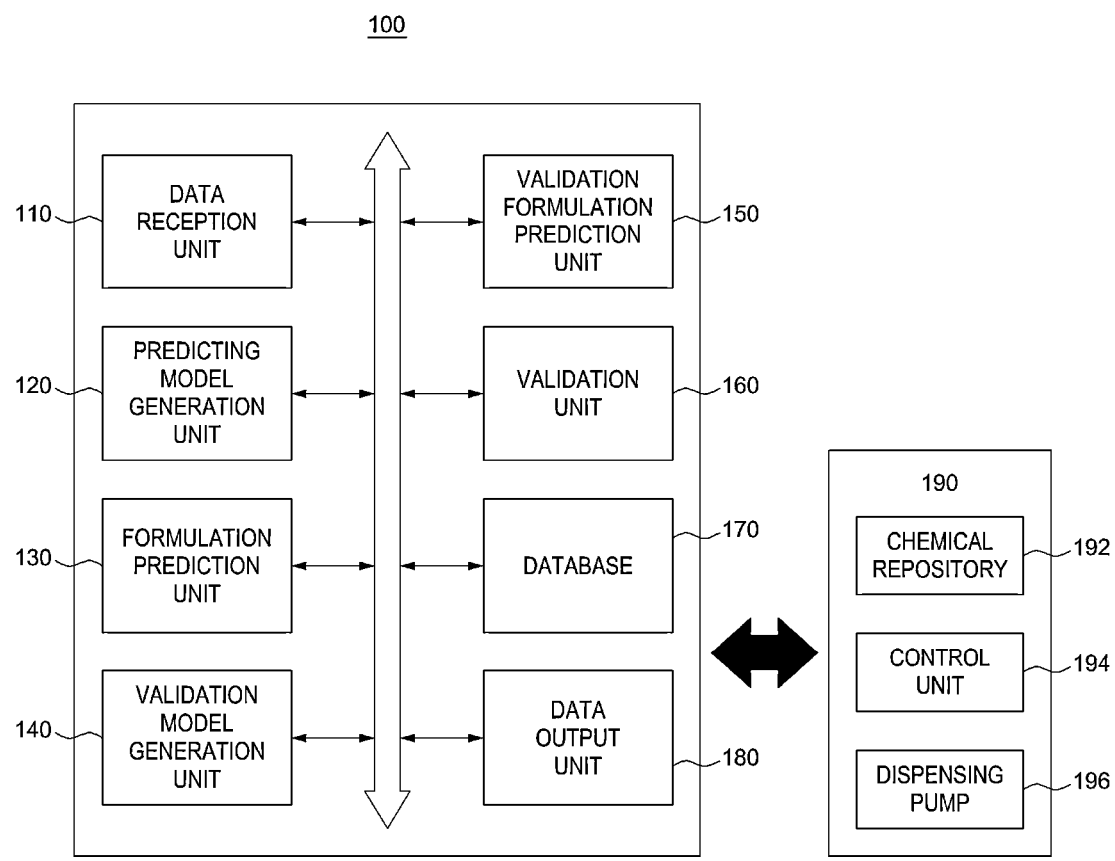
FIG. 1 is a block diagram illustrating a schematic configuration of an automated chemical formulation apparatus according to an embodiment of the present invention.

Hereinafter, the present invention will be described with reference to the accompanying drawings. However, the present invention may be embodied in several different forms, and thus is not limited to the embodiments described herein. Further, in order to clearly describe the present invention in the drawings, parts irrelevant to the description are omitted, and similar reference symbols are attached to similar parts throughout the specification.

Throughout the specification, when a part is described to be "linked (connected, in contact, or coupled)" with another part, this description includes not only the case of being "directly linked" but also the case of "indirectly linked" with another member interposed therebetween. In addition, when a part is described to "include" a certain component, this description means that other components may be further included, rather than excluding other components, unless otherwise stated.

The terminology used herein is used merely to describe specific embodiments, and is not intended to limit the present invention. The singular expression includes the plural expression unless the context clearly dictates otherwise. In the present specification, it should be understood that a term such as "include" or "have" is intended to designate that a feature, number, step, operation, component, part, or a combination thereof described in the specification is present, and the term does not preclude a possibility of presence or addition of one or more other features, numbers, steps, operations, components, parts, or combinations thereof.

Hereinafter, preferred embodiments are presented to help the understanding of the present invention. However, these are merely illustrative of the present invention, and it is apparent to those skilled in the art that various changes and modifications are possible within the scope and idea of the present invention. Further, it goes without saying that such changes and modifications fall within the scope of the appended claims.

Hereinafter, the present invention will be described in more detail with reference to the accompanying drawings illustrating embodiments of the present invention.

FIG. 1 is a block diagram illustrating a schematic configuration of an automated chemical formulation apparatus according to an embodiment of the present invention.

Referring to FIG. 1, an AI-based automated chemical formulation apparatus 100 according to an embodiment of the present invention may include a data reception unit 110, a predicting model generation unit 120, a formulation prediction unit 130, a validation model generation unit 140, a validation formulation prediction unit 150, and a validation unit 160, and may further include a database 170 and a data output unit 180. The automated chemical formulation apparatus 100 according to the embodiment of the present invention may further include a chemical dispensing device 190.

The data reception unit 110 may collect or receive a input chemical material dataset including chemical material information, chemical composition information, chemical formulation information, and/or chemical property information of the chemical formulation. In the input chemical material dataset, information other than the above-mentioned information may be added when the information is required for deriving a chemical formulation, or a part of the above-mentioned information may be excluded. The input chemical material dataset can be reduced in dimension and complexity of input data by weighting a principal variable or a principal component using feature importance or principal component analysis (PCA).

The predicting model generation unit 120 may train a first machine learning model using the input chemical material dataset to generate a predicting model for predicting a chemical formulation based on target property information of a target material. Here, a "target material" refers to a chemical material exhibiting a physical property specified by a user. A "target property" refers to one or more features required for a chemical material to be obtained by the user, and may be one or more of physical and/or chemical features. The first machine learning model may use one of a support vector machine (SVM) or XGboost (XGB) as a classification model. In another embodiment of the present invention, as the first machine learning model, other models from Sklearn and/or XGBoost libraries or a neural network model may be used instead of the classification model. However, the present invention is not limited thereto.

The input chemical material dataset is split into a training dataset and a validation dataset based on a criterion predetermined by the user, and a ratio thereof may be 80:20 in an embodiment of the present invention. However, the ratio is not limited thereto. After the first machine learning model is set, the model is trained using a normalized training dataset in the first chemical material dataset, and the trained model can be validated using the validation dataset. In an embodiment of the present invention, the performance of the first machine learning model may be evaluated based on both prediction accuracies of input features of the training dataset and the validation dataset. The performance of the first machine learning model may be evaluated based on receiver operating characteristics (ROC).

The formulation prediction unit 130 may set a boundary condition based on the input chemical material dataset, and generate a new input dataset including at least one of chemical material information, chemical composition information, and chemical formulation information within the boundary condition. Thereafter, the formulation prediction unit 130 may input the new input dataset to the predicting model, and set one or more predetermined pieces of target property information to perform prediction, thereby deriving and outputting chemical formulation data of a first group.

The formulation prediction unit 130 may generate the new input dataset using a pseudo-random number generator (pRDG) within the boundary condition. The formulation prediction unit 130 may set a boundary condition for grouping discovery of a chemical formulation newly optimized to refine data generation. When setting the boundary condition, it is possible to set boundary conditions that are the maximum and minimum values of a predetermined chemical material input feature, or to arbitrarily set boundary conditions that define parameter spaces in which the pRDG generates reasonable features required for the target material by the users. The formulation prediction unit 130 may generate new input parameters (R1, R2, R3, ..., Rn) with the real space (Rn) of the nth dimension using the pRDG. To minimize search for Rn, boundary conditions for pseudo-random number generation are set to obtain an input $x_i^{new} \sim w \, U[\min(x_i^{old}), \max(x_i^{old})]$, where $U(a,b)$ represents a uniform distribution and can vary randomly between 0 and 1.

The formulation prediction unit 130 may input the generated new input dataset $x_i^{new}$ to the predicting model to perform prediction, thereby obtaining $y_i^{new}$, which is a candidate group of a chemical formulation solution. The formulation prediction unit 130 can continuously repeat the process until a certain number of satisfied solutions $y_i^{new}$ is found. Among the solutions ($y_i^{new}$), $y_i^{new}$ satisfying the predetermined one or more pieces of target property information may be derived and output as chemical formulation data of a first group.

The validation model generation unit 140 may generate a validation model by training a second machine learning model different from the first machine learning model using the same input chemical material dataset. The second machine learning model can use one of a SVM or XGB as a classification model, and it is preferable to select a model different from the first machine learning model. In another embodiment of the present invention, the first machine learning model may be other models from Sklearn and/or XGBoost libraries or neural network models instead of the classification model. However, the present invention is not limited thereto. The second machine learning model may also be trained using the normalized training dataset in the input chemical material dataset, and then the trained model may be validated using the validation dataset. The performance of the second machine learning model may be evaluated based on both the prediction accuracies of the input features of the training dataset and the validation dataset. The performance of the second machine learning model may be evaluated based on the ROCs.

The validation formulation prediction unit 150 may input the new input dataset $x_i^{new}$ generated by the formulation prediction unit 130 to the validation model, and set the same predetermined one or more pieces of target property information as that used for the predicting model to perform prediction, thereby outputting a second group of chemical formulation data.

The validation unit 160 may compare and validate the first group of chemical formulation data with the second group of chemical formulation data, and select and derive matching data as chemical formulation data of a third group corresponding to the predetermined one or more pieces of target property information. The first group of chemical formulation data having a greater degree of dispersion compared to the second group of chemical formulation data may be excluded. Through this configuration, the present invention can minimize the variety of validation by experiments as in the conventional technology and increase a confidence level of machine learning prediction. In an embodiment of the present invention, the chemical formulation solutions in the third group of chemical formulation data may be ranked in suitability according to a predetermined condition.

The database 170 may store at least one or more of the first chemical material data, the predicting model, the validation model, and the chemical formulation data of the first to third groups, and further store other information including various parameters generated in an automated chemical formulation process.

The data output unit 180 may transmit some or all of the third group of chemical formulation data derived from the validation unit 160 to the chemical dispensing device 190. In addition, the data output unit 180 may transfer or output some or all of the third group of chemical formulation data to the internal components of the automated chemical formulation apparatus 100 or transmit some or all of the third group of chemical formulation data to an external connected device.

The chemical dispensing device 190 may include a chemical repository 192, a control unit 194, and a dispensing pump 196. A plurality of chemical repositories 192 may store individual component materials constituting the target chemical material. The control unit 194 can control inflow and/or outflow of the individual component materials in the chemical repositories 192 to and/or from the dispensing pump 196 based on the third group of chemical formulation data by the chemical dispensing device 190. The dispensing pump 196 may include a stepper motor and a peristaltic pump, and based on the third group of chemical formulation data, the dispensing pump 196 may disperse and supply the individual component materials at an accurate volume and/or weight.

According to an embodiment of the present invention, in the automated chemical formulation apparatus, components of the predicting model generation unit 120, the formulation prediction unit 130, the validation model generation unit 140, the validation formulation prediction unit 150, and the validation unit 160 may be included in a single computing device or processor, or may be separated and included in a plurality of computing devices or processors.

Figure 2:
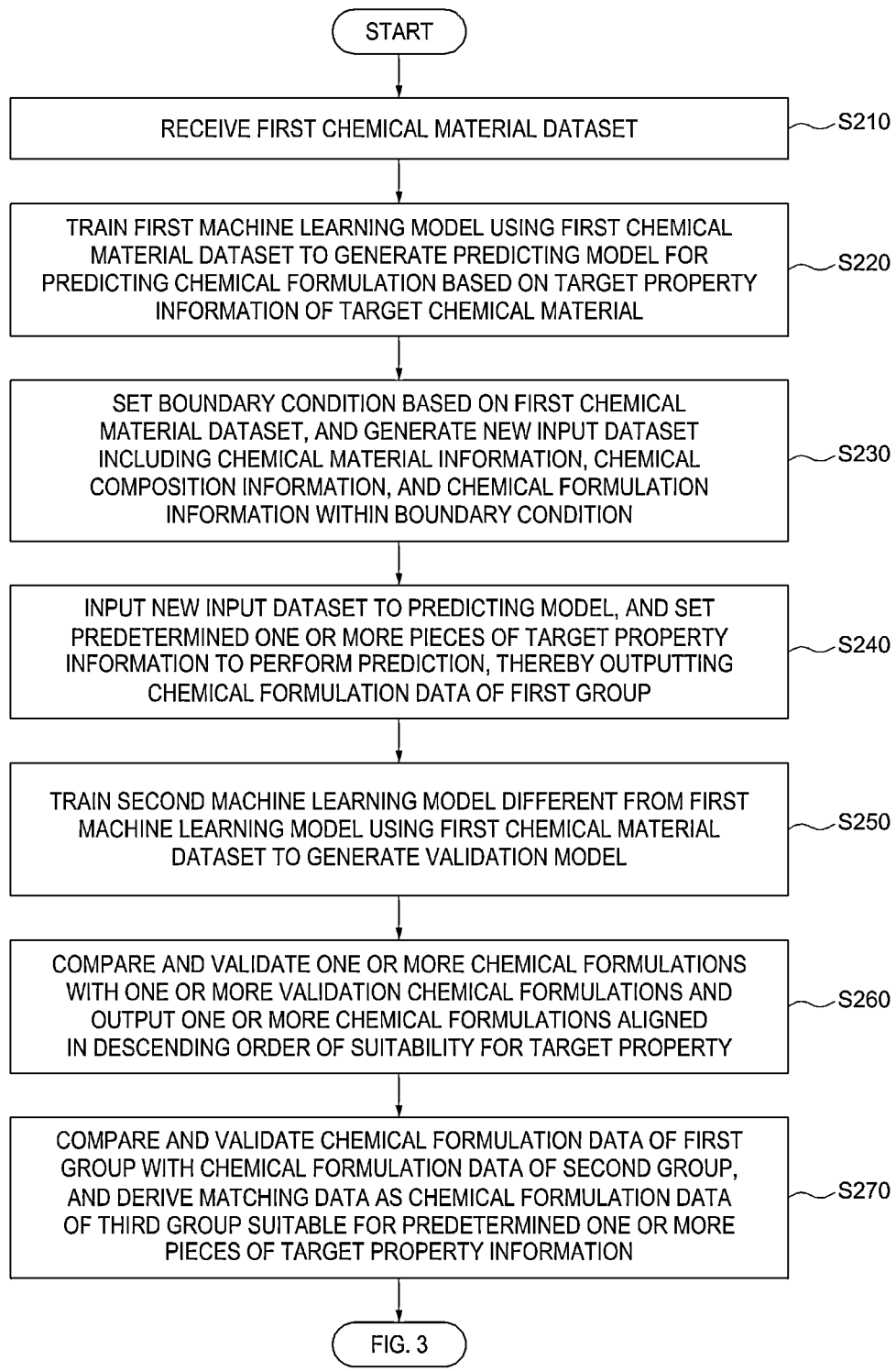
FIG. 2 is a flowchart of an automated chemical formulation method according to an embodiment of the present invention.
Figure 3:
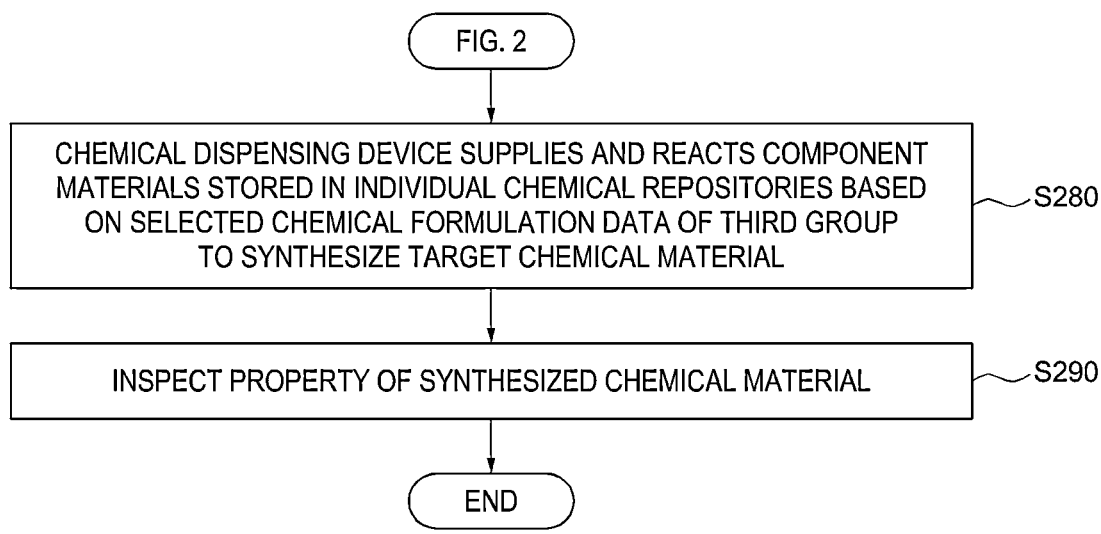
FIG. 3 is a flowchart of steps according to an embodiment of the present invention that can be added to the automated chemical formulation method of FIG. 2.

FIG. 2 is a flowchart of an automated chemical formulation method according to an embodiment of the present invention which may be performed by a computing device. FIG. 3 is a flowchart of steps according to an embodiment of the present invention that can be added to the automated chemical formulation method of FIG. 2.

Referring to FIG. 2, step S210 to step S270 of the automated chemical formulation method according to the embodiment of the present invention are as follows.

In step S210, an input chemical material dataset including chemical material information, chemical composition information, chemical formulation information and property information thereof is collected or received. In the input chemical material dataset, information other than the above-mentioned information may be added when the information is required for deriving a chemical formulation, or a part of the above-mentioned information may be excluded.

In step S220, the first machine learning model is trained using the input chemical material dataset to generate a predicting model for predicting a chemical formulation based on target property information of a target chemical material. The first machine learning model may use one of a SVM or XGB as a classification model. In another embodiment of the present invention, as the first machine learning model, other models from Sklearn and/or XGBoost libraries or a neural network model may be used instead of the classification model. However, the present invention is not limited thereto. The input chemical material dataset can be reduced in dimension and complexity of the input data by weighting the principal variables or principal components using feature importance or principal component analysis (PCA).

In step S230, a boundary condition is set based on the input chemical material dataset, and a new input dataset including at least one of the chemical material information, the chemical composition information, and the chemical formulation information is generated within the boundary condition. In step S230, the new input dataset may be generated using the pRDG within the boundary condition. When setting the boundary condition, it is possible to set boundary conditions that are the maximum and minimum values of a predetermined chemical material input feature, or to arbitrarily set boundary conditions that define parameter spaces in which the pRDG generates reasonable features required for the target material by the users. When generating the new input dataset, new input parameters (R1, R2, R3, . . . , Rn) with the real space (Rn) of the nth dimension may be generated using the pRDG. To minimize search for Rn, boundary conditions for pseudo-random number generation are set to obtain an input $x_i^{new} \sim U[\min(x_i^{new}), \max(x_i^{new})]$, where $U(a,b)$ represents a uniform distribution and can vary randomly between 0 and 1.

In step S240, the new input dataset is input to the predicting model, and predetermined one or more pieces of target property information are set to perform prediction, thereby outputting chemical formulation data of the first group. In step S240, the generated new input dataset $x_i^{new}$ is input to the predicting model to perform prediction, so that $y_i^{new}$, which is a candidate group of a chemical formulation solution can be obtained. In this instance, it is possible to continuously repeat the process until a certain number of satisfied solutions ($y_i^{new}$) is found. Among the solutions ($y_i^{new}$), $y_i^{new}$ satisfying the predetermined one or more pieces of target property information may be derived and output as chemical formulation data of the first group.

In step S250, a second machine learning model different from the first machine learning model is trained using the input chemical material dataset to generate a validation model. The second machine learning model can be one of a SVM or XGB as a classification model, and it is preferable to select a model different from the first machine learning model. In another embodiment of the present invention, the first machine learning model may use other models from Sklearn and/or XGBoost libraries or neural network models instead of the classification model. However, the present invention is not limited thereto.

In step S260, the new input dataset is input to the validation model, and the predetermined one or more pieces of target property information are set to perform prediction, thereby outputting chemical formulation data of the second group.

In step S270, the first group of chemical formulation data is compared and validated with the second group of chemical formulation data, and matching data is selected and derived as chemical formulation data of a third group suitable for the predetermined one or more pieces of target property information. The chemical formulation solutions in the third group of chemical formulation data may be ranked in suitability according to a predetermined condition.

According to an embodiment of the present invention, the predicting model generation step (S220), the new input dataset generation step (S230), the first group chemical formulation data prediction step (S240), the validation model generation step (S250), the second group chemical formulation data prediction step (S260), and the third group chemical formulation data prediction step (S270) may be performed by a single computing device or processor, or may be separated and performed by a plurality of computing devices or processors.

Referring to FIG. 3, the following steps may be added to the automated chemical formulation method of FIG. 2, which will be described below.

In step S280, the chemical dispensing device supplies and reacts component materials stored in individual chemical repositories based on the third group of chemical formulation data selected and derived in step S280 of FIG. 2 to synthesize a target chemical material. Referring to FIG. 1, the chemical dispensing device 190 includes the chemical repository 192, the control unit 194, and the dispensing pump 196, and the control unit 194 can control inflow and/or outflow of the individual component materials stored in the plurality of chemical repositories 192 to and/or from the dispensing pump 196 based on the third group of chemical formulation data by the chemical dispensing device 190. The dispensing pump 196 may include a stepper motor and a peristaltic pump, and based on the third group of chemical formulation data, the dispensing pump 196 may disperse and supply the individual component materials at an accurate volume and/or weight.

In step S290, physical properties or defects of the synthesized chemical material are inspected.

Figure 4:
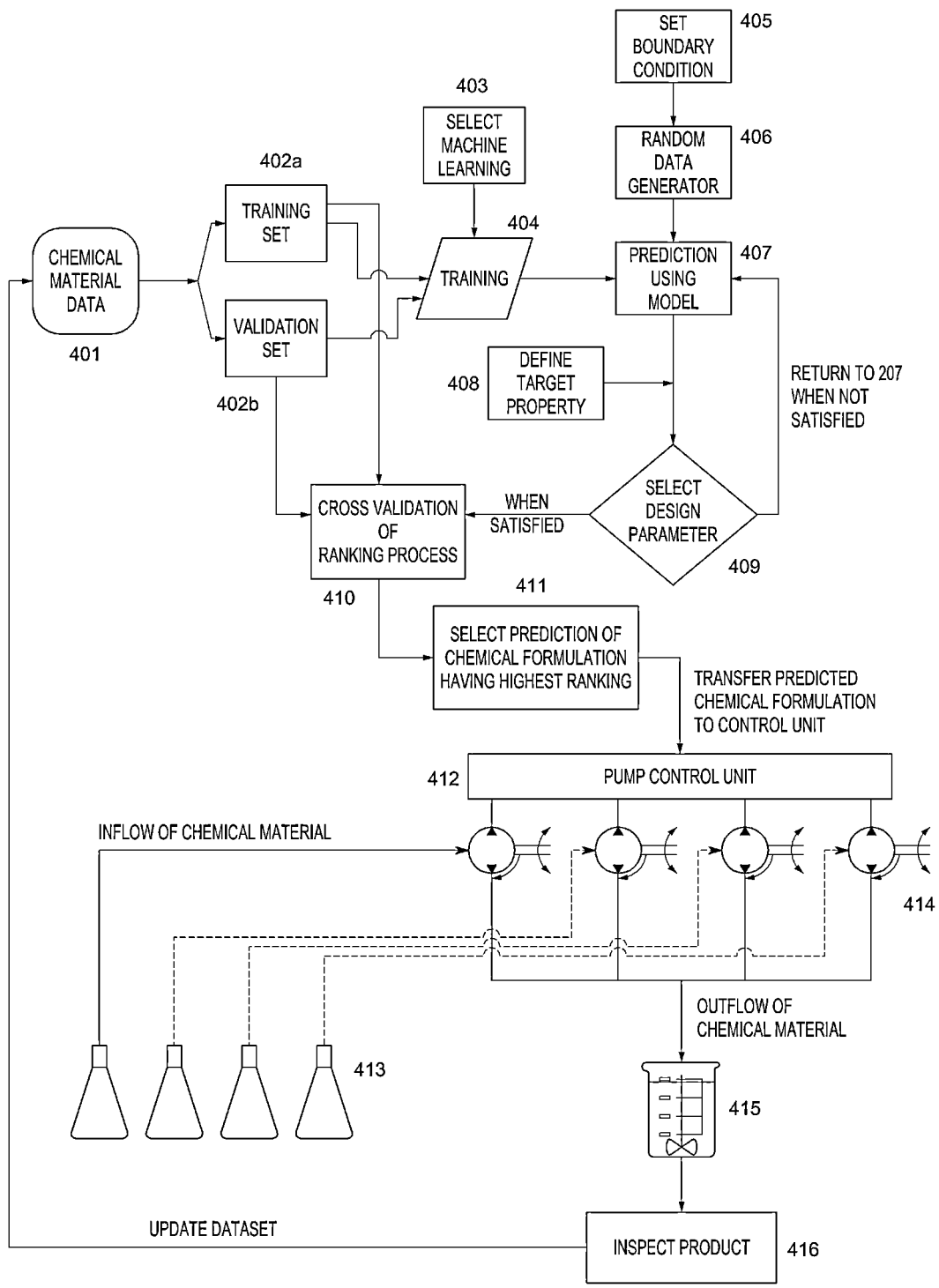
FIG. 4 is a flowchart illustrating an automated polyurethane formulation method according to an embodiment of the present invention.

FIG. 4 is a flowchart illustrating a method of automatically deriving a formulation of polyurethane (PU) by the automated chemical formulation method according to an embodiment of the present invention.

Referring to FIG. 4, in step 401, for polyurethane, a polyurethane-related dataset including chemical material information, chemical composition information, chemical formulation information, and chemical property information according to the information is received as an input parameter for training the first learning machine model.

An exemplary list of formulations for polyurethane is shown in Table 1. In the present embodiment, eleven chemical materials used for the polyurethane formulations, namely polyol, dibutyltin dilaurate (DBTL), glycerol, triethylamine, (TEA), pentamethyldiethylenetriamine (PMDETA), 1,4-diazabicyclo[2,2,2]octane (DABCO), N,N-dimethylcyclohexylamin (DMCHA), cyclopentene, silicon surfactant, water, and isocyanate were included as component materials R1 to R11. Even though major reactions for polyurethane formulations are dominated by isocyanate-polyol and isocyanate-water, the complexity of the chemical reaction was elevated with a combination of different catalysts, chain extenders, and surfactants. A timing feature, such as a time at which a next chemical material begins to flow into a reactor, may be included as an input parameter. Due to the flexibility of this approach, it is possible to increase the number of variables for each problem.

TABLE 1

| Trial | Polyol (g) | DBTL (g) | Glycerol (g) | Triethylamine (g) | PMDETA (ml) | DABCO (g) | DMCHA (ml) |
|---|---|---|---|---|---|---|---|
| 1 | 17.884 | 0.659 | 0 | 0.164 | 0.5 | 0.051 | 0.5 |
| 2 | 9.6 | 0 | 0 | 0 | 0 | 0 | 0.5 |
| 3 | 10.72 | 0 | 0 | 0 | 0.5 | 0 | 0 |
| 4 | 15.543 | 0.457 | 0 | 0 | 0 | 0 | 0 |
| 5 | 11.056 | 0 | 0 | 0.23 | 0 | 0 | 0 |
| 6 | 15.159 | 0 | 0 | 0 | 0 | 0.175 | 0 |
| 7 | 10.308 | 0 | 0 | 0 | 0 | 0 | 0 |
| 8 | 10.804 | 0.195 | 0 | 0.205 | 0 | 0 | 0 |
| 9 | 10.332 | 0.14 | 1.433 | 0 | 0.2 | 0 | 0 |
| 10 | 10.413 | 0.166 | 1.731 | 0 | 0.25 | 0 | 0 |
| 11 | 11.463 | 0 | 0 | 0.192 | 0.25 | 0 | 0 |
| 12 | 11.642 | 0 | 1.657 | 0.197 | 0.25 | 0 | 0 |
| 13 | 10.719 | 0.251 | 1.183 | 0.166 | 0 | 0 | 0 |
| 14 | 10.261 | 0.264 | 1.163 | 0.27 | 0 | 0 | 0 |
| 15 | 10.069 | 0 | 1.16 | 0.303 | 0 | 0 | 0.25 |
| 16 | 10.363 | 0 | 1.261 | 0.283 | 0 | 0 | 0 |
| 17 | 10.93 | 0 | 1.204 | 0.361 | 0.1 | 0 | 0 |
| 18 | 10.136 | 0.279 | 1.067 | 0 | 0.1 | 0 | 0 |
| 19 | 10.905 | 0.278 | 1.268 | 0 | 0 | 0 | 0.25 |
| 20 | 10.429 | 0.298 | 1.103 | 0.346 | 0 | 0 | 0.2 |
| 21 | 10.063 | 0.273 | 1.05 | 0 | 0.1 | 0 | 0 |
| 22 | 11.029 | 0.291 | 1.283 | 0 | 0.1 | 0 | 0 |
| 23 | 10.503 | 0.364 | 1.431 | 0.294 | 0.1 | 0 | 0 |
| 24 | 10.764 | 0.257 | 1.159 | 0.275 | 0.1 | 0 | 0 |
| 25 | 10.729 | 0.215 | 0.941 | 0.079 | 0.08 | 0 | 0.05 |
| 26 | 10.96 | 0.222 | 0.941 | 0.201 | 0.08 | 0 | 0.05 |
| 27 | 10.216 | 0.275 | 1.125 | 0.18 | 0.05 | 0 | 0 |
| 28 | 10.855 | 0.272 | 1.219 | 0.215 | 0.1 | 0 | 0 |

| Trial | Cyclopentene (ml) | Silicone Surfactant (g) | Water (ml) | TDI (g) | Height (mm) | Speed (s) | Condition |
|---|---|---|---|---|---|---|---|
| 1 | 0 | 1.907 | 2 | 22.188 | 210 | 1 | FAIL |
| 2 | 5.966 | 1.433 | 2 | 4.563 | 40 | 57.27 | FAIL |
| 3 | 0 | 1.279 | 1 | 8.357 | 200 | 1 | FAIL |
| 4 | 0 | 1.77 | 3 | 8.458 | 120 | 69.8 | FAIL |
| 5 | 0 | 1.609 | 3 | 4.747 | 90 | 119.25 | FAIL |
| 6 | 0 | 2.436 | 2 | 6.346 | 110 | 41.523 | FAIL |
| 7 | 0 | 1.283 | 0.5 | 5.115 | 85 | 188.05 | FAIL |
| 8 | 0 | 1.283 | 0.5 | 5.115 | 115 | 78.725 | SUCCESS |
| 9 | 0 | 1.295 | 2 | 4.937 | 125 | 69.72 | FAIL |
| 10 | 4.892 | 1.408 | 3 | 6.125 | 130 | 110.77 | FAIL |
| 11 | 0 | 1.157 | 1 | 5.431 | 160 | 10.77 | FAIL |
| 12 | 0 | 1.777 | 1 | 5.34 | 145 | 66.34 | FAIL |

TABLE 1-continued

| 13 | 0 | 1.7 | 0.5 | 5.092 | 85 | 50.05 | FAIL |
|---|---|---|---|---|---|---|---|
| 14 | 0 | 0.715 | 1 | 8.545 | 150 | 25.99 | SUCCESS |
| 15 | 0 | 0.811 | 1 | 9.924 | 230 | 17.22 | FAIL |
| 16 | 0 | 0.888 | 1 | 10.174 | 120 | 297.65 | FAIL |
| 17 | 0 | 0.806 | 1 | 8.54 | 135 | 72.75 | FAIL |
| 18 | 0 | 0.925 | 1 | 8.374 | 210 | 14.32 | FAIL |
| 19 | 0 | 0.846 | 1 | 9.395 | 250 | 11.55 | SUCCESS |
| 20 | 0 | 1.088 | 1 | 9.21 | 220 | 11.73 | FAIL |
| 21 | 0 | 0 | 1 | 8.418 | 100 | 24.67 | FAIL |
| 22 | 0 | 0.315 | 1 | 8.349 | 165 | 12.57 | FAIL |
| 23 | 0 | 1.619 | 1 | 8.764 | 180 | 13.84 | FAIL |
| 24 | 0 | 1.056 | 1 | 8.506 | 155 | 13.51 | FAIL |
| 25 | 0.13 | 1.155 | 1.14 | 7.098 | 190 | 25.25 | FAIL |
| 26 | 0.13 | 1.118 | 1.14 | 8.277 | 205 | 15.93 | FAIL |
| 27 | 0 | 0.914 | 1 | 8.517 | 215 | 25.79 | SUCCESS |
| 28 | 0 | 0.91 | 1 | 8.721 | 165 | 10.11 | FAIL |

<Exemplary Input Parameters>

The polyurethane-related dataset can be reduced in dimension and complexity of the input data by weighting the principal variable or principal component using feature importance or principal component analysis (PCA).

Figure 5:
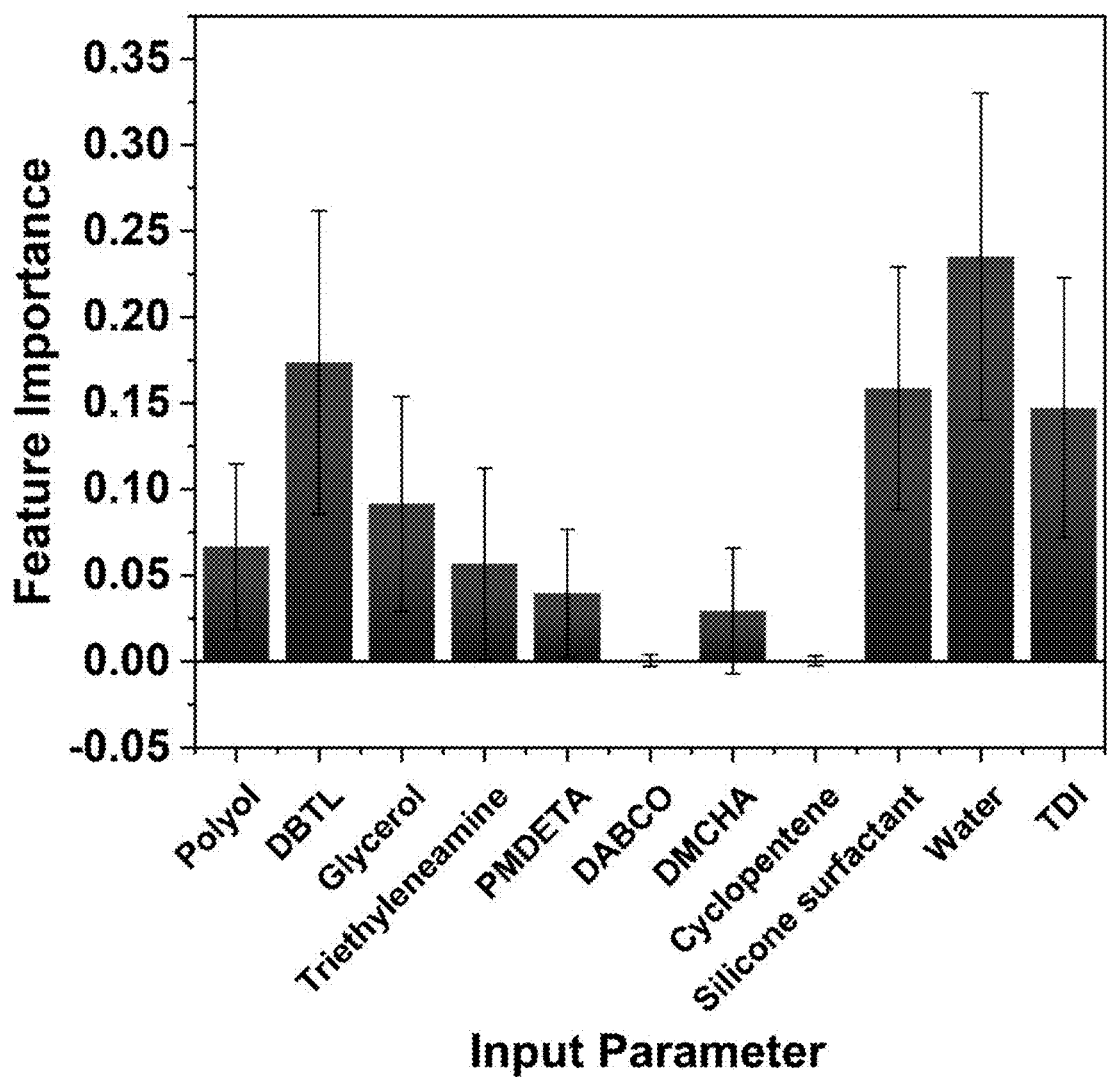
FIG. 5 is a graph illustrating an example of feature importance of input parameters of a specific chemical material input to the automated chemical formulation apparatus according to the embodiment of the present invention.

FIG. 5 is a graph illustrating an example of feature importance of input parameters of a specific chemical material input to the automated chemical formulation apparatus according to the embodiment of the present invention. Prior to machine learning training, polyurethane-related data collected from a previous experiment was analyzed. FIG. 5 illustrates the feature importance of the input parameters, that is, components, and it was found that catalyst (DBTL), water, silicone surfactant, and curing agent (TDI) are four most important features associated with the success of polyurethane synthesis. Using this information, these input parameters are more highly weighted while setting a boundary condition of the predicting model to discover a new formulation.

Referring back to FIG. 4, in step 402 (402a and 402b), the polyurethane-related data is split into a training dataset and a validation dataset at a ratio of 80:20. However, this ratio may be adjusted according to the need of the user.

In step 403, the first machine learning model is selected, and in the present embodiment, the SVM is selected as the classification model. However, other models from Sklearn and/or XGBoost libraries or a neural network model may be used instead of the classification model.

However, the present invention is not limited thereto.

In step 404, the SVM model is trained using the training dataset of step 402a to generate a predicting model for predicting a desired polyurethane formulation. Before training the SVM model, it is assumed that all features are centered at zero with variance of equal magnitude, and input vectors thereof are normalized by a standard scalar method.

$$Z_i = (x_i - \mu)/s \quad (1)$$

Here, $Z_i$ denotes a normalized vector, $x_i$ denotes an input vector, and p and s denote an average and a standard deviation of a training vector in an nth-order real space Rn. Target y is coded as a binary system of 0 and 1. With given input vectors, the goal of the SVM is to find w and b so that $sign(w^T \phi(x)+b)$ is accurate for most samples. During training, the classified SVM solves the following.

$$\min_{w,b,s} \frac{1}{m} w^T w + C \sum_{i=1}^{n} \varepsilon_i \quad (2)$$

Subject to $y_i(w^T \phi(x_i + b) \geq 1 - \varepsilon_i; \varepsilon_i \geq 0$

In the present embodiment, a margin of a hyperplane is maximized by minimizing $w^T w$ which allows several vectors to be at a distance $\varepsilon_i$ from an exact boundary thereof. When optimization problems are solved, the classifier VM has the following formula.

$$\Sigma_i y_i \alpha_i K(x_i, x) + b \quad (3)$$

Here, α is a double coefficient and K is a kernel function. In the present embodiment, a nonlinear radial basis function (RBF: $\exp(-\gamma \|x - x'\|^2)$) is used. γ has the form of $1/(nf \times X_v)$, where nf denotes the number of features, and $X_v$ denotes a variance of x. Since γ is currently processed with the SKlearn library, the optimization of penalty C can be easily performed using a grid survey method. A SVM validation model was generated by training an XGB (XGboost) model with a training dataset in the polyurethane-related data generated in step 402 and validating performance using a validation dataset. The performance of the predicting model generated through training of the SVM model was validated using the validation dataset generated in step 402b.

Figure 6:
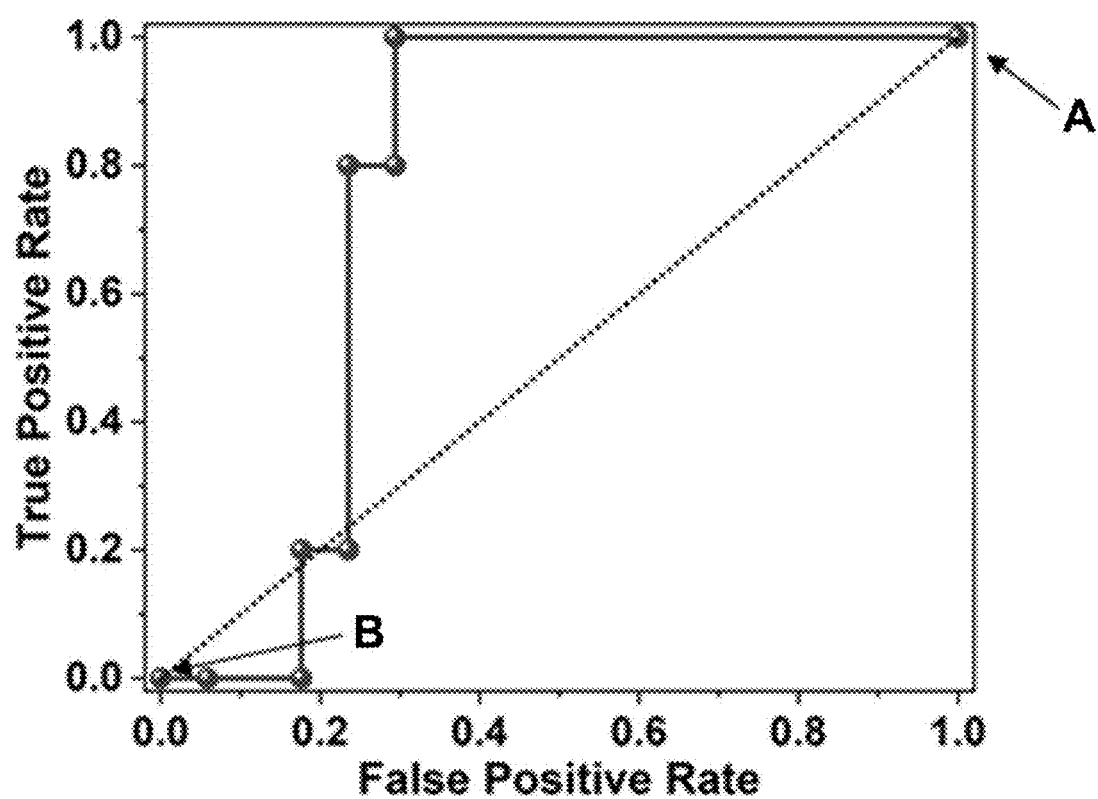
FIG. 6 is a graph illustrating a receiver operating characteristic (ROC) curve of a predicting model generated according to an embodiment of the present invention.

FIG. 6 is a graph illustrating an ROC curve of a polyurethane predicting model generated according to an embodiment of the present invention. The classification performance of the generated predicting model may be evaluated using an ROC, as illustrated in FIG. 6. In the present embodiment, a Boolean classifier was used to predict the 'Fail' and 'Success' formulations of the polyurethane required. Here, the success formulation means that the polyurethane foam, which is a desired final shape, has physical properties that can maintain a shape without undergoing collapse, significant shrinkage, and/or transformation into powder. Each point on the ROC of the predicting model corresponds to a formulation result. A at the top right and B at the bottom left represent a complete 'success' formulation and a complete 'fail' formulation, respectively. A classifier having full performance has a true positive rate of 1 and a false positive rate of 0. In the present embodiment, a predicting model trained using a polyurethane-related dataset from previous experiments was generated to have an area under the curve (AUC) of 0.76 for the ROC.

In steps 405 and 406, a boundary condition was set based on the polyurethane-related dataset, and the new input dataset was generated using the pRDG within the boundary condition. In the present embodiment, boundary conditions that are the maximum and minimum values of the predetermined input feature variables were set when setting the boundary conditions. The pRDG may be used to generate new input parameters (R1, R2, R3, ..., Rn) having the real space (Rn) of the nth dimension. To minimize search for Rn, boundary conditions for pseudo-random number generation may be set to obtain an input $x_i^{new} \sim U[\min(x_i^{old}), \max(x_i^{old})]$, where U(a,b) represents a uniform distribution and can vary randomly between 0 and 1.

In steps 407 to 409, the new input dataset was input to the predicting model, and predetermined one or more pieces of target property information were set to perform prediction, thereby outputting polyurethane formulation data of a first group. The generated new input dataset $x_i^{new}$ was input to the predicting model to perform prediction, thereby acquiring $y_i^{new}$ which is a candidate group of a polyurethane formulation solution. In this instance, it is possible to continuously repeat the process until a certain number of satisfied solutions ($y_i^{new}$) is found. Among the solutions ($y_i^{new}$), $y_i^{new}$ satisfying the predetermined one or more pieces of target property information may be derived and output as the polyurethane formulation data of the first group. In the present embodiment, using the predicting model, 30 new polyurethane formulations having a higher success rate than that of other formulations were derived as polyurethane formulation data of the first group.

In step 410, a second machine learning model different from the first machine learning model was trained using the polyurethane-related dataset to generate a validation model. The second machine learning model can be one of a SVM or XGB as a classification model, and a different model from the first machine learning model is selected. In the present embodiment, XGB was used as the second machine learning model. The validation model was generated by training the XGB model using a training dataset in the polyurethane-related data generated in step 402 and validating performance using a validation dataset. Polyurethane formulation data of a second group was derived by inputting the new input dataset $x_i^{new}$ generated in step 406 to the generated validation model and setting the same predetermined one or more pieces of target property information of step 408 as that used for the predicting model to perform prediction.

In step 411, the polyurethane formulation data of the first group may be compared and validated with the polyurethane formulation data of the second group to select and derive matching data as polyurethane formulation data of a third group corresponding to the predetermined one or more pieces of target property information. Table 2 below shows predicted polyurethane formulation data matched as a required target proper.

TABLE 2

| Polyol | DBTL | Glycerol | Triethylamine | PMDETA | DABCO | DMCHA | Cyclopentene | Silicone surfactant | Water | TDI | Target | Filtering option |
|---|---|---|---|---|---|---|---|---|---|---|---|---|
| 10.291 | 0.273 | 1.271 | 0.282 | 0.146 | 0 | 0 | 0 | 0.104 | 0.774 | 9.095 | Success | Fail |
| 11.866 | 0.568 | 0.835 | 0.124 | 0.154 | 0 | 0 | 0 | 0.451 | 0.876 | 10.927 | Success | Success |
| 10.422 | 0.574 | 1.065 | 0.36 | 0.164 | 0 | 0 | 0 | 0.007 | 0.737 | 10.547 | Success | Fail |
| 11.132 | 0.116 | 1.341 | 0.366 | 0.047 | 0 | 0 | 0 | 0.165 | 0.832 | 10.937 | Success | Fail |
| 11.218 | 0.43 | 1.275 | 0.203 | 0.058 | 0 | 0 | 0 | 1.11 | 0.718 | 9.967 | Success | Fail |
| 11.523 | 0.488 | 1.39 | 0.261 | 0.051 | 0 | 0 | 0 | 0.997 | 0.808 | 9.987 | Success | Fail |
| 11.165 | 0.088 | 1.176 | 0.345 | 0.033 | 0 | 0 | 0 | 0.066 | 0.857 | 9.438 | Success | Fail |
| 10.62 | 0.373 | 1.151 | 0.299 | 0.114 | 0 | 0 | 0 | 0.251 | 0.815 | 10.44 | Success | Fail |
| 10.418 | 0.234 | 1.436 | 0.16 | 0.143 | 0 | 0 | 0 | 0.709 | 0.921 | 9.322 | Success | Fail |
| 11.598 | 0.524 | 0.547 | 0.079 | 0.05 | 0 | 0 | 0 | 0.165 | 0.54 | 10.829 | Success | Fail |
| 10.804 | 0.324 | 0.974 | 0.137 | 0.091 | 0 | 0 | 0 | 0.189 | 0.625 | 9.825 | Success | Fail |
| 11.861 | 0.359 | 1.481 | 0.16 | 0.052 | 0 | 0 | 0 | 0.508 | 0.663 | 9.543 | Success | Fail |
| 10.609 | 0.562 | 1.492 | 0.223 | 0.046 | 0 | 0 | 0 | 0.836 | 0.876 | 10.707 | Success | Fail |
| 11.642 | 0.212 | 1.174 | 0.178 | 0.145 | 0 | 0 | 0 | 0.803 | 0.711 | 10.601 | Success | Fail |
| 10.287 | 0.535 | 0.503 | 0.294 | 0.141 | 0 | 0 | 0 | 0.581 | 0.628 | 9.322 | Success | Fail |
| 11.685 | 0.33 | 0.771 | 0.79 | 0.127 | 0 | 0 | 0 | 0.144 | 0.628 | 10.726 | Success | Fail |
| 11.158 | 0.134 | 0.894 | 0.183 | 0.142 | 0 | 0 | 0 | 0.574 | 0.512 | 9.309 | Success | Fail |
| 10.212 | 0.053 | 1.125 | 0.018 | 0.113 | 0 | 0 | 0 | 0.759 | 0.602 | 10.9 | Success | Fail |
| 11.473 | 0.228 | 1.388 | 0.042 | 0.167 | 0 | 0 | 0 | 1.019 | 1.049 | 9.563 | Success | Fail |
| 11.477 | 0.468 | 0.848 | 0.014 | 0.003 | 0 | 0 | 0 | 0.82 | 0.531 | 9.956 | Success | Fail |
| 11.021 | 0.122 | 0.548 | 0.361 | 0.17 | 0 | 0 | 0 | 1.252 | 0.96 | 10.377 | Success | Success |
| 10.079 | 0.347 | 0.733 | 0.395 | 0.002 | 0 | 0 | 0 | 0.9 | 0.684 | 10.763 | Success | Fail |
| 11.392 | 0.56 | 0.692 | 0.035 | 0.069 | 0 | 0 | 0 | 0.927 | 0.549 | 9.63 | Success | Fail |
| 10.407 | 0.161 | 1.167 | 0.177 | 0.151 | 0 | 0 | 0 | 0.965 | 1.007 | 9.804 | Success | Fail |
| 11.085 | 0.585 | 0.507 | 0.199 | 0.085 | 0 | 0 | 0 | 0.346 | 0.631 | 9.588 | Success | Fail |
| 11.804 | 0.569 | 0.76 | 0.011 | 0.053 | 0 | 0 | 0 | 0.121 | 0.711 | 9.339 | Success | Fail |
| 11.233 | 0.222 | 1.274 | 0.207 | 0.081 | 0 | 0 | 0 | 0.649 | 1.093 | 10.581 | Success | Fail |
| 10.711 | 0.558 | 0.758 | 0.233 | 0.115 | 0 | 0 | 0 | 0.422 | 1.051 | 10.476 | Success | Fail |
| 10.68 | 0.464 | 1.118 | 0.099 | 0.1 | 0 | 0 | 0 | 0.105 | 0.869 | 10.66 | Success | Fail |
| 11.669 | 0.131 | 1.448 | 0.134 | 0.138 | 0 | 0 | 0 | 1.158 | 0.918 | 10.018 | Success | Fail |

<Output Polyurethane Formulation Data Matched as Required Target Property>

Table 2 shows 30 pieces of formulation data classified as success in the target item of the second column from the right, which were derived as the polyurethane formulation data of the first group by the predicting model. Of the 30 pieces of formulation data of Table 2, two pieces of formulation data classified as success in the filtering option item of the first column on the right side are data succeeding in matching in a filtering process through matching with the polyurethane formulation data of the second group derived from the validation model and become the polyurethane formulation data of the third group. Referring to FIG. 1, the data is transmitted to the control unit 194 of the chemical dispensing device 190. The control unit 194 drives the dispensing pump 196 to provide each component material stored in the chemical repository 192 according to the polyurethane formulation data of the third group. In the present embodiment, an Arduino UNO was used for the control unit 194. When preparation and mixing of the component materials is complete, a mixture thereof is manually or automatically stirred for 10 seconds before a desired shape of polyurethane foam is generated to achieve a desired property of a target chemical material, that is, the polyurethane foam.

As described above, the present invention can generalize complex and seemingly uncorrelated parameters and transmit a prediction to the control unit of the automated dispensing device to provide a solution capable of reducing trial and error due to experiments, etc. of researchers and increasing quality and research speed. Such an automated chemical formulation apparatus and method can be applied to other applications such as nanoparticle synthesis, cosmetic or pharmaceutical formulation, etc.

The embodiments described above may be implemented by a hardware component, a software component, and/or a combination of a hardware component and a software component. For example, the system, the apparatus, the method, and the components described in the embodiments may be implemented using one or more general-purpose computers or special-purpose computers such as a processor, a controller, a central processing unit (CPU), a graphics processing unit (GPU), an arithmetic logic unit (ALU), a digital signal processor, a microcomputer, a field programmable gate array (FPGA), a programmable logic unit (PLU), a microprocessor, application specific integrated circuits (ASICS), a server, or any other computing device capable of executing and responding to instructions.

The automated chemical formulation method according to the embodiment of the present invention may be implemented in the form of program instructions that can be executed through various computer means and recorded in a computer-readable medium. The computer-readable medium may include program instructions, data files, data structures, etc. alone or in combination. The program instructions recorded on the medium may be specially designed and configured for the embodiment, or may be known and available to those skilled in the art of computer software. The hardware device may be configured to operate as one or more software modules to perform the operations of the embodiments, and vice versa.

Even though the embodiments have been described with reference to the limited drawings as described above, various modifications and variations are possible from the above description by those of ordinary skill in the art. For example, an appropriate result may be achieved even when the described techniques are performed in a different order from that in the described method, and/or the described components of the system, structure, apparatus, circuit, etc. are united or combined in a different form from that in the described method, or replaced or substituted by other components or equivalents.

According to the present invention, formulation data suitable for a target property of a desired chemical material is predicted through a machine learning model trained based on chemical material-related big data including existing experimental data, and a prediction result is filtered based on a matching process of a prediction result of a different machine learning model, thereby providing an effect of allowing derivation and validation of a chemical formulation exhibiting a desired target property with high accuracy and efficiency while minimizing or not requiring a trial-and-error search such as a search based on empirical rules of researchers or a time-consuming and expensive experiment in deriving the chemical formulation.

According to the present invention, a chemical formulation having a high success rate is predicted based on two different machine learning models, and predicted formulation data is automatically transmitted to a dispensing device for chemical synthesis so that a chemical material can be manufactured. In this way, it is possible to minimize time-consuming trial and error due to an experiment of a researcher, etc. and to increase the quality and research speed, and it is possible to provide an automated chemical formulation system that is economical while exhibiting high accuracy.

It should be understood that effects of the present invention are not limited to the above-described effects, and include all effects that can be inferred from the configuration of the invention described in the detailed description or claims of the present invention.

The scope of the present invention is indicated by the following claims, and all changes or modifications derived from the meaning and scope of the claims and equivalents thereof should be construed as being included in the scope of the present invention.

100: automated chemical formulation apparatus, 110: data reception unit, 120: predicting model generation unit, 130: formulation prediction unit, 140: validation model generation unit, 150: validation formulation prediction unit, 160: validation unit, 170: database, 180: data output unit, 190: chemical dispensing device, 192: chemical repository, 194: control unit, 196: dispensing pump

What is claimed is:

1. An automated chemical formulation apparatus comprising:
   a computing device, comprising:
      a data reception unit configured to receive an input chemical material dataset of a chemical material including chemical material information, chemical composition information, chemical formulation information and property information of the chemical material;
      a predicting model generation unit configured to train a first machine learning model using the input chemical material dataset to generate a predicting model for predicting a chemical formulation based on target property information of a target material;
      a formulation prediction unit configured to set a boundary condition based on the input chemical material dataset, generate a new input dataset including at least one of new chemical material information, new chemical composition information, and new chemical formulation information within the boundary condition, input the new input dataset to the predicting model, and set predetermined one or more pieces of target property information to perform prediction, thereby outputting a first group of chemical formulation data;
      a validation model generation unit configured to train a second machine learning model different from the first machine learning model using the input chemical material dataset to generate a validation model;
      a validation formulation prediction unit configured to input the new input dataset to the validation model, and set the predetermined one or more pieces of target property information to perform prediction, thereby outputting a second group of chemical formulation data; and
      a validation unit configured to compare and verify the first group of chemical formulation data with the second group of chemical formulation data to derive matching data as a third group of chemical formulation data corresponding to the predetermined one or more pieces of target property information; and
   a chemical dispensing device comprising a control unit, a dispensing pump and individual chemical repositories and the control unit of the chemical dispensing device configured to perform a control operation to supply component materials stored in individual chemical repositories through the dispensing pump based on the third group of chemical formulation data to synthesize a target chemical material.

2. The apparatus according to claim 1, further comprising an inspection device configured to inspect a property of the target chemical material synthesized using the chemical dispensing device.

3. The apparatus according to claim 1, wherein when setting the boundary condition, the formulation prediction unit sets boundary conditions that are maximum and minimum values of a predetermined chemical material input feature.

4. The apparatus according to claim 1, wherein the formulation prediction unit generates the new input dataset using a pseudo-random number generator (pRDG) within the boundary condition.

5. The apparatus according to claim 1, wherein the input chemical material dataset is reduced in dimension and complexity of input data by weighting using feature importance or principal component analysis (PCA).

6. The apparatus according to claim 1, wherein the first machine learning model uses one of a support vector machine (SVM) or XGboost (XGB).

7. An automated chemical formulation method performed by a computing device and a chemical dispensing device comprising a control unit, a dispensing pump and individual chemical repositories, the method comprising:
receiving, using the computing device, an input chemical material dataset of a chemical material including chemical material information, chemical composition information, chemical formulation information and property information of the chemical material;
training, using the computing device, a first machine learning model using the input chemical material dataset to generate a predicting model for predicting a chemical formulation based on target property information of a target material;
setting, using the computing device, a boundary condition based on the input chemical material dataset, and generating a new input dataset including at least one of new chemical material information, new chemical composition information, and new chemical formulation information within the boundary condition;
inputting, using the computing device, the new input dataset to the predicting model, and setting predetermined one or more pieces of target property information to perform prediction, thereby outputting a first group of chemical formulation data;
training, using the computing device, a second machine learning model different from the first machine learning model using the input chemical material dataset to generate a validation model;
inputting, using the computing device, the new input dataset to the validation model, and setting the predetermined one or more pieces of target property information to perform prediction, thereby outputting a second group of chemical formulation data;
comparing and verifying, using the computing device, the first group of chemical formulation data with the second group of chemical formulation data to derive matching data as a third group of chemical formulation data corresponding to the predetermined one or more pieces of target property information; and
performing, using the control unit of the chemical dispensing device, a control operation to supply component materials stored in individual chemical repositories through the dispensing pump based on the third group of chemical formulation data to synthesize a target chemical material.

8. The method according to claim 7, further comprising inspecting a property of the target chemical material synthesized using the chemical dispensing device.

9. The method according to claim 7, wherein the generating of the new input dataset includes setting boundary conditions that are maximum and minimum values of a predetermined chemical feature.

10. The method according to claim 7, wherein the generating of the new input dataset includes generating the new input dataset using a pRDG within the boundary condition.

11. The method according to claim 7, wherein the input chemical material dataset is reduced in dimension and complexity of input data by weighting a principal variable or a principal component using feature importance or PCA.

12. The method according to claim 7, wherein the first machine learning model uses one of an SVM or XGB.

13. A non-transitory computer-readable storage medium stored with computer instructions, wherein the computer instructions, when executed, are configured to cause a computing device and a chemical dispensing device comprising a control unit, a dispensing pump and individual chemical repositories to perform an automated chemical formulation method, the method comprising:
receiving, using the computing device, an input chemical material dataset of a chemical material including chemical material information, chemical composition information, chemical formulation information and property information of the chemical material;
training, using the computing device, a first machine learning model using the input chemical material dataset to generate a predicting model for predicting a chemical formulation based on target property information of a target material;
setting, using the computing device, a boundary condition based on the input chemical material dataset, and generating a new input dataset including at least one of new chemical material information, new chemical composition information, and new chemical formulation information within the boundary condition;
inputting, using the computing device, the new input dataset to the predicting model, and setting predetermined one or more pieces of target property information to perform prediction, thereby outputting a first group of chemical formulation data;
training, using the computing device, a second machine learning model different from the first machine learning model using the input chemical material dataset to generate a validation model;
inputting, using the computing device, the new input dataset to the validation model, and setting the predetermined one or more pieces of target property information to perform prediction, thereby outputting a second group of chemical formulation data;
comparing and verifying, using the computing device, the first group of chemical formulation data with the second group of chemical formulation data to derive matching data as a third group of chemical formulation data corresponding to the predetermined one or more pieces of target property information; and
performing, using the control unit of the chemical dispensing device, a control operation to supply component materials stored in individual chemical repositories through the dispensing pump based on the third group of chemical formulation data to synthesize a target chemical material.

\* \* \* \* \*